US007376700B1

(12) United States Patent
Clark et al.

(10) Patent No.: US 7,376,700 B1
(45) Date of Patent: May 20, 2008

(54) PERSONAL COACHING SYSTEM FOR CLIENTS WITH ONGOING CONCERNS SUCH AS WEIGHT LOSS

(75) Inventors: Paul T. Clark, Wellesley, MA (US); Margaret A. Moore, Wellesley, MA (US)

(73) Assignee: Wellcoaches Corporation, Wellesley, MA (US)

( * ) Notice: Subject to any disclaimer, the term of this patent is extended or adjusted under 35 U.S.C. 154(b) by 1077 days.

(21) Appl. No.: 09/628,607

(22) Filed: Jul. 31, 2000

Related U.S. Application Data

(63) Continuation-in-part of application No. 09/415,622, filed on Oct. 12, 1999, now abandoned, which is a continuation-in-part of application No. 09/379,448, filed on Aug. 23, 1999, now abandoned.

(51) Int. Cl.
*G06F 15/16* (2006.01)
*G06F 50/00* (2006.01)
*G06F 15/02* (2006.01)
*G07G 1/14* (2006.01)
*G06Q 10/00* (2006.01)
*G06F 9/46* (2006.01)
*G07G 1/00* (2006.01)

(52) U.S. Cl. .................. 709/204; 709/203; 709/319; 705/2; 705/9; 705/14

(58) Field of Classification Search ............. 709/203, 709/204, 219, 227; 705/2, 3, 8, 9, 14; 706/45
See application file for complete search history.

(56) References Cited

U.S. PATENT DOCUMENTS

| 5,369,570 | A | * | 11/1994 | Parad | 705/8 |
| 5,596,994 | A | * | 1/1997 | Bro | 600/545 |
| 5,722,418 | A | * | 3/1998 | Bro | 600/545 |
| 5,748,907 | A | * | 5/1998 | Crane | 705/2 |
| 5,855,920 | A | * | 1/1999 | Chein | 424/568 |
| 5,911,132 | A | * | 6/1999 | Sloane | 705/3 |
| 6,039,688 | A | * | 3/2000 | Douglas et al. | 600/300 |
| 6,081,786 | A | * | 6/2000 | Barry et al. | 705/3 |
| 6,124,854 | A | * | 9/2000 | Sartain et al. | 715/716 |
| 6,161,095 | A | * | 12/2000 | Brown | 705/2 |
| 6,192,394 | B1 | * | 2/2001 | Gutfreund et al. | 709/204 |
| 6,256,664 | B1 | * | 7/2001 | Donoho et al. | 709/204 |
| 6,278,999 | B1 | * | 8/2001 | Knapp | 707/9 |
| 6,285,983 | B1 | * | 9/2001 | Jenkins | 705/10 |
| 6,289,353 | B1 | * | 9/2001 | Hazlehurst et al. | 707/102 |
| 6,292,786 | B1 | * | 9/2001 | Deaton et al. | 705/14 |
| 6,325,632 | B1 | * | 12/2001 | Chao et al. | 434/322 |
| 6,334,778 | B1 | * | 1/2002 | Brown | 434/258 |
| 6,336,133 | B1 | * | 1/2002 | Morris et al. | 709/204 |
| 6,336,136 | B1 | * | 1/2002 | Harris | 709/219 |
| 6,356,940 | B1 | * | 3/2002 | Short | 709/217 |
| 6,363,393 | B1 | * | 3/2002 | Ribitzky | 707/102 |
| 6,381,557 | B1 | * | 4/2002 | Babula et al. | 702/183 |
| 6,405,175 | B1 | * | 6/2002 | Ng | 705/14 |
| 6,430,542 | B1 | * | 8/2002 | Moran | 705/36 |
| 6,434,531 | B1 | * | 8/2002 | Lancelot et al. | 705/3 |
| 6,434,572 | B2 | * | 8/2002 | Derzay et al. | 707/104.1 |
| 6,442,590 | B1 | * | 8/2002 | Inala et al. | 709/204 |
| 6,460,036 | B1 | * | 10/2002 | Herz | 707/10 |
| 6,463,079 | B2 | * | 10/2002 | Sundaresan et al. | 370/468 |
| 6,484,196 | B1 | * | 11/2002 | Maurille | 709/206 |
| 6,499,114 | B1 | * | 12/2002 | Almstead et al. | 714/25 |
| 6,510,430 | B1 | * | 1/2003 | Oberwager et al. | 707/10 |
| 6,546,372 | B2 | * | 4/2003 | Lauffer | 705/8 |
| 6,581,038 | B1 | * | 6/2003 | Mahran | 705/3 |
| 6,659,916 | B1 | * | 12/2003 | Shea | 482/57 |
| 6,760,748 | B1 | * | 7/2004 | Hakim | 709/204 |
| 6,792,412 | B1 | * | 9/2004 | Sullivan et al. | 706/25 |
| 6,820,235 | B1 | * | 11/2004 | Bleicher et al. | 715/501.1 |
| 6,873,965 | B2 | * | 3/2005 | Feldman et al. | 705/10 |
| 6,915,336 | B1 | * | 7/2005 | Hankejh et al. | 709/219 |
| 7,117,189 | B1 | * | 10/2006 | Nichols et al. | 706/45 |
| 2001/0041990 | A1 | * | 11/2001 | Javitt | 705/2 |
| 2002/0010616 | A1 | * | 1/2002 | Itzhaki | 705/9 |
| 2002/0013836 | A1 | * | 1/2002 | Friedman et al. | 709/223 |
| 2002/0035506 | A1 | * | 3/2002 | Loya | 705/14 |
| 2002/0062225 | A1 | * | 5/2002 | Siperco | 705/2 |
| 2002/0064767 | A1 | * | 5/2002 | McCormick et al. | 434/396 |
| 2002/0065682 | A1 | * | 5/2002 | Goldenberg | 705/2 |

(Continued)

FOREIGN PATENT DOCUMENTS

EP 1427190 A1 * 6/2004

(Continued)

OTHER PUBLICATIONS

Roberts, Sherry, "Brain Waves. (using computers to receive an education by conducting classes online0" Compute! Issue 133, Sep. 1991, p.18.*

(Continued)

*Primary Examiner*—Melvin H. Pollack
(74) *Attorney, Agent, or Firm*—Clark & Elbing LLP

(57) ABSTRACT

The invention features a method for coaching a plurality of clients, involving providing multiple coaches and assigning a personal coach to each client. Information is received from each client particular to an ongoing concern of the client, e.g., weight loss, and, based on that information, the coach devises a set of recommendations that are transmitted to the client, starting the coaching relationship.

32 Claims, No Drawings

U.S. PATENT DOCUMENTS

| | | | |
|---|---|---|---|
| 2003/0023473 A1* | 1/2003 | Guyan et al. | 705/9 |
| 2003/0049595 A1* | 3/2003 | Stuppy et al. | 434/350 |
| 2003/0055679 A1* | 3/2003 | Soll et al. | 705/2 |
| 2003/0187683 A1* | 10/2003 | Kirchhoff et al. | 705/1 |
| 2003/0208380 A1* | 11/2003 | Honeycutt | 705/2 |
| 2004/0208475 A1* | 10/2004 | Ohmura et al. | 386/4 |
| 2006/0010014 A1* | 1/2006 | Brown | 705/2 |

FOREIGN PATENT DOCUMENTS

| | | | |
|---|---|---|---|
| JP | 2000348013 A * | 12/2000 | |
| JP | 2002215804 A * | 8/2002 | |
| JP | 203345909 A * | 12/2003 | |
| WO | WO 9904043 A1 * | 1/1999 | |
| WO | WO 2003067373 A2 * | 8/2003 | |
| WO | WO 2006071892 A2 * | 7/2006 | |

OTHER PUBLICATIONS

Single P.B. and Muller, C. B. "When Email and Mentoring Unite: The Implementation of a Nationwide Elecronic Mentoring Program," American Society for Traning and Development (ASTD) In Action Series, 2001, pp. 107-122.*

Muller, C.B. and Single, P.B. "MentorNet: Leveraging Technology to Increase the Numbers of Women in Engineering and Science," Intl Symposium on Technology and Society, Jul. 31, 1999, p. 110.*

Taylor, Jeff. "The Continental Classroom: Teaching Labour Studi s Online" Labor Studies Journal 21(1), Spring 1996.*

Bellinger, Robert. "HP's Mentoring Project Grows International in Size," Times, Dec. 30, 1998.*

Bludnicki, Mary. "Supporting Virtual Learning for Adult Students," T.H.E. Journal Online (Technological Horizons in Education) Jun. 1998.*

"Matchmaker.com Announces Free Back-to-School Site for College Students, " Business Wire, Aug. 18, 1999.*

Rovito, Rich. "GE Med Boosts Rapid Diagnosis: T ams with Hospital to Streamline Imaging Information," The Business Journal of Milwauke , Exclusive Reports, Feb. 21, 2003.*

Select Pages from WebMD: Check Systems, Clinical Chart. Dec. 14, 2004.*

Spielberg, Alissa R. "Online Without a Net: Physician-Patient Communication by Electronic Mail," American Journal of Law and Medicine. vol. 25, Issue 2/3, 1999, p. 267-296.*

"Nutri/system Online" Web Pages from Internet Archive, Apr. 27, 1999, pp. 1-11.*

"iVillage.com" Web Pages from Internet Archive, Apr. 22, 1999, pp. 1-2.*

"Jenny Craig" Web Pages from Internet Archive, Oct. 9, 1999, pp. 1-3.*

"Weight Watchers" Web Pages from Internet Archive, May 8, 1999, pp. 1-21.*

"HealthGal" pages from Internet Archive, Sep. 28, 2004, pp. 1-6.*

"Weight Loss Buddy" Web Pages from Internet Archive, Oct. 17, 2003, pp. 1-20.*

"Life in Motion" Web Pages from Internet Archive, Aug. 30, 2004, pp. 1-21.*

Figallo, Cliff. "iVillage: Investing in Community and Banking on Trust," EContent Magazine, Jun. 1, 2002, pp. 1-3.* www.toptutors.com.

* cited by examiner

PERSONAL COACHING SYSTEM FOR CLIENTS WITH ONGOING CONCERNS SUCH AS WEIGHT LOSS

CROSS REFERENCE TO RELATED APPLICATIONS

This application is a continuation-in-part of Clark et al. U.S. Ser. No. 09/415,622, "Internet Coaching," filed Oct. 12, 1999 now abandoned, which in turn is a continuation-in-part of Clark U.S. Ser. No. 09/379,448, filed Aug. 23, 1999 now abandoned.

BACKGROUND OF THE INVENTION

This invention relates to a high priority of many adult North Americans is to look good and feel good. Most have taken some steps in their adult lives to look and feel better. The fact is that most fail to stick with these steps. They also fail to look and feel their best, most of the time.

There is a wealth of information and ideas available from books, television, friends, family, doctors, and now the Internet. It is daunting, however, for most people to find and sift through the enormous amount of conflicting information and then devise a program of steps that fit into their lifestyles. Even more difficult is the development and execution of a personalized and staged plan over their lifetimes. Hardest of all is sustaining motivation on one's own.

The Web has thousands of sites providing current information and advice on health, fitness, nutrition, and wellness. Many such sites are described in a book entitled WebDoctor, by Vicki and Richard Sharp (St. Martin's Griffin, New York, 1998), hereby incorporated by reference.

A few examples of interactive, health-related Web sites are given below.

Mayo Health Oasis sponsored by the Mayo clinic, provides health information and includes Ask Mayo, permitting users to ask questions of medical experts.

American Heart Association: heart disease information and online risk assessment test for heart disease.

Basal Metabolism: the program asks for individual information (e.g., weight and activity level) and returns daily caloric and protein, fat, and carbohydrate requirements.

The Eat Well Calculator: the individual reports details of food intake and online experts "tell you how well you're doing."

LifeMatters: "An ongoing conversation about taking charge of one's health and well-being for a life that is empowered, fulfilled and profoundly related." The site is an interactive forum that draws on various experts.

Phys Nutrition for Normal People: an interactive online magazine for women; the site's personal nutritionist provides customized diet plans.

Ask An Expert: Health: a directory of health experts, including their Web sites so individuals can ask them questions.

Health Status Questionnaire: online version of Rand's 36-question survey for self-evaluation of health.

You First: personalized online health risk assessment report, including recommendations to improve health.

HomeArts Winning at Losing: a four-week weight loss plan for women, including interactive program to calculate calories burned during various activities.

A Man's Life: includes an interactive personal trainer called the Big Sweat, where the individual can request advice for training particular body parts.

Magic Stream Journal: includes an online counseling service available 24 hours a day.

Metanoia Guide to Internet Mental Health Services: provides access to counselors who provide online mental health services.

While a great deal of useful information is contained in sites such as those described above, they are usually unsuccessful in causing lasting positive changes in the lives of large numbers of people.

SUMMARY OF THE INVENTION

The invention uses the power of the Internet, combined with long-term, one-on-one motivational coaching, to bring about positive changes in many lives, and to sustain and build on those changes over time.

The invention features a personalized, interactive, progressive, Internet-based coaching system. The system of the invention can be used to help individuals ("clients") address their ongoing concerns, such as health and fitness, financial planning, career development, elder care, and menopause. The system can be illustrated by describing the health and fitness program that employs the unique concepts of the invention. These principles are applicable to any of the programs encompassed by the invention.

As in all of the programs to which the methods of the invention are applicable, the health and fitness program includes, as a key component, assigning to each client a personal coach who interacts with the client, via the Internet, to improve the health and fitness of the individual. The first step is to establish the baseline health, fitness, stress, weight, and nutrition facts for the client. This is done by having the client complete a questionnaire that inquires into the client's general health (including the presence of disease states such as diabetes and coronary artery disease), eating habits, stress levels, daily schedules, patterns of exercise, and readiness to change in each area.

The coach proposes guidelines and initial health, nutrition, fitness, and wellness goals based on the baseline information provided by the client in the questionnaire. The coach then works with the client online to agree the short-term and longer-term goals, and helps the client take small steps each week toward the goals.

To maintain early gains in health and fitness, and in particular to build on those gains to achieve the next level, the client must, we believe, develop a long-term relationship with her personal online coach. The coach becomes, over time, intimately familiar with her client's life habits as they evolve and change in response to coaching. Only a coach who has worked with a client over time can provide the trust-based motivation necessary to achieve lasting, progressive improvements in health and fitness. The coach knows, respects, and cares about each of her clients. She cheers her client's victories and helps her, in a positive way, understand and improve on the habits and behaviors that have stood in the way of her looking and feeling her best.

Another vital link in the motivational process that is essential for real, lasting change is the client's ability to rely on a regularly scheduled one-on-one online coaching slot with her coach. This fixed schedule achieves several important objectives.

First, a schedule eliminates the uncertainty that would ensue with random or unscheduled sessions.

Second, the scheduled sessions give the client something to look forward to: she knows that at 3 pm twice per week, for example, she will have the chance (over the Internet) to tell her coach, with whom she has developed a bond of mutual respect and caring, of her gains over the past two days. She also knows that this scheduled session provides her the opportunity to talk to her coach online about any new (or chronic) health or wellness-related problems, and find out what her coach suggests to address the problems. Immediate solutions, of course, are not always possible, and are in any event not the only dividends of coaching; the client, like any other human being, wants to be listened to by someone she knows, and who cares about her.

Finally, a fixed schedule relieves the client from a large portion of the motivational burden to keep going on the program: the client does not need to summon the will, or find that she cannot summon the will, to contact a counselor at a given time. That component of her motivation is already fixed, for the foreseeable future, and the client is freed from struggling with that issue anew every time she thinks she might benefit from counseling. She can instead focus her efforts on maximizing the benefits of each scheduled coaching session.

Interaction by the Internet provides advantages for coaching that are not possible by other means. Individuals with concerns are often embarrassed and reserved about discussing their problems in person or by telephone. Where a client's concerns relate to personal appearance, she may be uncomfortable being looked at by a coach. Individuals will often say things online that they wouldn't say in person, or even on the telephone. The Internet mode of contact can facilitate more intimate, open, and honest discussion of difficult issues, enabling a more effective ongoing interaction with a coach.

The coaching system of the invention is applicable not just to health-related issues. Indeed, the invention can be used to coach clients on any issue that, for at least a period of time, or during a life stage, is ongoing in nature. Examples are: relationships (family, romantic, professional), stress and anxiety, depression, pregnancy, addiction, e.g. to alcohol or tobacco, child rearing, careers, menopause and andropause, chronic diseases such as diabetes, retirement, management of finances, elder care, e.g. caring for relatives with Alzheimer's disease, caring for disabled persons, and caring for pets.

Accordingly, the invention features a method by which a company provides interactive, Internet-based, ongoing advice and coaching to a plurality of individuals, involving: a) providing a cadre of trained coaches, all of whom interact with clients via the Internet using as guidance a coaching manual and training provided by the company and/or its affiliates; b) at some stage in the method prior to step f), below, assigning, from the cadre of coaches, an online personal coach to each individual; c) receiving from the individual information particular to an ongoing concern of the individual (e.g., weight loss or cardiac rehabilitation); d) based on the information provided in step c), devising a set of recommendations for the individual pertinent to the individual's ongoing concern; e) transmitting recommendations of step d) to the individual via the Internet; f) having transmitted to the individual's coach, via the Internet, particularized information from the individual pertaining to the ongoing concern of the individual, wherein the information includes reportage of events occurring in the life of the individual subsequent to the transmittal of the recommendations of step e); g) based on the information received by the individual's coach in step f), having the coach devise a further set of recommendations for the individual pertinent to the ongoing concern of the individual; h) transmitting the recommendations of step g) to the individual via the Internet; and i) repeating steps f-h) multiple times.

In preferred embodiments, the online interactions between the individual and the coach of steps f-h) include real-time dialogues; and the interactions occur at scheduled times. Coaching sessions occur either entirely online, or have one or more online components, including one, two, or all of "chat," Internet telephone, Internet audio other than telephony, and video formats. Conventional telephony can in some instances be used in conjunction with the Internet components.

A feature that can be added to the coaching process to provide an operant conditioning component that can enhance progress in meeting client goals is to provide incentives for reaching goals. Thus, the company provides rewards, or points redeemable for rewards, for achievement of goals. For example, if a client loses ten pounds over a period of three months, consistent with goals the coach and client have set for the client, the company gives the client a reward such as a piece of fitness equipment or apparel, or points in the company's system that are redeemable for high-quality items that market research has shown clients want, including new items of clothing that accentuate improvements in appearance. These items are selected by the client from catalogues based on arrangements with apparel or other companies, or from the company's own catalogue.

Points in the reward system can be earned as well in at least two other ways: 1) clients are awarded points for agreeing to communicate (usually by the Internet), with prospective clients; this helps build the business in an effective way, with testimonials; and 2) clients are awarded points for being on time for or not missing some predetermined number of scheduled coaching appointments.

This system of rewards for achieved goals is in an important sense the antithesis of incentive systems of other health-related programs. For example, in the Jenny Craig weight-loss system, it is the client, not the company, that is rewarded for the reaching of client goals; the client pays the company one dollar for every pound the client loses. This in effect is the opposite of operant conditioning; the benefit of weight loss is accompanied by a monetary penalty. The system of the invention, in contrast, sends the client a consistent message: reaching the client's goals is accompanied by a further benefit, awarded by the company. Thus the client has two sources of motivation for reaching her goals, and is more likely to do so.

The company, according to one preferred method of the invention, charges clients fees for the coaching service provided. The method includes, optionally, additional sources of revenue as well. One such source is selling advertising space on the Web site the company maintains to inform the public of the company's coaching service and attract new clients. Another revenue source arises from the sales of products through the company's Web site, whereby the sales generate a commission for the company based on the volume of sales. To maintain the integrity and reputation of the coaching process, it is essential that all of the products in both the advertising and product tie-in revenue streams be of the highest quality, and be the types of products that are consistent with the client's program, the company's philosophy, and guidelines as set out in the coach manual.

There will also be provided a public-access Web site that describes the coaching program and tells visitors to the site how to become clients or coaches. The site will post frequent announcements of new program-related breakthroughs, and as well may carry advertising for high-quality program-related products.

Another optional feature that can enhance the commitment, loyalty and team spirit of the coaches is a chat room to which only the coaches, but not the clients or the general public, have access. The coaches' chat room can serve as an after-hours retreat for the coaches, and provide them an opportunity to compare notes on client issues and the coaching process.

In addition, the program can include a chat room to which only the clients, but not the coaches or the general public, have access. This site provides the clients with the chance to support each other in their struggles to overcome problems they have in common. In addition, relationships, including romantic ones, can be fostered through such a site, and indeed can be formalized thorough a Web site-specific introduction program.

Both the clients' chat room and the coaches' chat room may feature, from time to time, guest "speakers," who are authorities on relevant topics.

Some clients will be hesitant to sign up for the coaching program because they do not place a high enough priority on their own health and fitness. To reach such clients, the company may offer gift certificates to individuals who purchase the coaching services for a spouse, child, family member, friend, or colleague.

An objective of the programs of the invention is to provide practical, personalized plans and ongoing, Internet-based coaching to help people improve their lives. One program, the "look better and feel better" program, helps clients lose weight, increase physical activity, reduce stress, improve their nutrition, and reduce their health risks.

Database and Manual

The "look better and feel better" program will draw on a large and comprehensive database of old and new approaches to improving health, fitness, and well-being. The database will be continually updated, with the aid of expert advisors. The database is used primarily for two purposes: 1) the development of a coach manual, which is continuously updated. Each coach has access to the manual, which is used both to train and test the coach prior to her beginning her coaching of clients, and as a reference for providing online recommendations to clients. The manual is a key component of the system, as it ensures uniformity of philosophy and substance from coach to coach in advising clients.

Coaches

Coaches will be recruited from a range of backgrounds. Preferably, they will be college educated, and have educational and/or work experience in fitness, health, nutrition, education, nursing, counseling, physical therapy, exercise physiology, or social work. Coaches will be chosen as well for their natural coaching ability, empathy, and integrity.

Client Files

An important advantage of providing one-on-one coaching via the Internet is that an electronic (i.e., digital) record can be kept of the goals that the coach and client set for the client, and the history of the client's meeting of those goals. In one preferred embodiment, a coaching session that takes advantage of the stored goals proceeds as follows.

The client and coach logon at the predetermined time, and recording (both audio taping and digital recording of text) of the session begins. A running clock appears on the screens of both client and coach. At the start of the session, both the client and the coach are viewing the same on-screen text listing the client's goals from the previous week or other period during which they had agreed on those goals; they use the present session, at least in part, to discuss whether the goals have been met, and strategies for meeting those that are still unmet. For example, the client may have had, as the previous week's goals, the following: 1. substitute, for night-time sweet snack, a low-calorie snack; 2. determine schedule of locally-offered yoga and step classes; 3. walk instead of drive to the train station five days in a row.

As the session begins, the coach's talking head appears on the client's screen; the coach and client talk via Internet telephony or telephone about the previous week's goals, the challenges in meeting some of them, goals for the next time period, and other remaining issues. Although the coach's face is visible to the client, the client can choose to be seen or not seen by the coach, allowing the client to maintain privacy and modesty (he can be sitting in the bathtub if he likes).

During or following the recorded session, one or both of client and coach type goals for the next time period (a week, bi-week, or month). This new goal text, along with the text of the previous goals, is stored in the client's electronic file; the file can be called up on the client's screen at any time between coaching sessions. This file allows the client to track her progress over time, and encourages the client to view her personal growth project in a manner similar to the way she would view a long-term assignment at work, i.e., tracking goals met and not met is in some respects an exercise in project management. The file acts not just as a long-term motivating force, but also as a reality check: the client can instantly check whether, six months ago, she really did weigh more than she does now.

The Business

As is described above, all of the coaches must pass the same training and testing, based on a common database and manual. The manual is created by a program development team that also manages and continually updates the database and manual.

Many or all of the coaches work from their homes, and can choose to work as many hours as they wish. There are no geographic limitations to their home locations; the only requirement is that they be able to travel to training and refresher sessions. The coaches are paid a percentage of the client fees based on a company schedule.

Once a coach has passed the training and testing, she is assigned a number of clients for whom she will serve as the online personal coach. The coaching of the client proceeds and evolves over time as described above, beginning, in most cases, with the development by the coach of an initial 3-month plan. This initial plan serves as the framework for the day-to-day coaching interactions, and is constantly being refined and built upon.

The client chooses the frequency of the coaching sessions, and might also choose from a selection of options for the duration of each session; generally, the sessions will be fifteen to thirty minutes long. Frequency and duration of coaching sessions can be adjusted by the client as her personal plan, goals, progress, and needs evolve.

Other embodiment are within the following claims.

What is claimed is:

1. A method by which a company provides interactive, ongoing coaching to a plurality of clients using non-e-mail-based Internet communication as well as e-mail based communications, said method comprising:
    a) providing multiple coaches who have access to a common web platform;
    b) at some stage in said method prior to step d), assigning a personal coach from said multiple coaches to each said client;

c) receiving from the client information particular to an ongoing personal, health-related concern of the client;

d) having the coach and client meet in real-time, scheduled coaching sessions;

e) having the coach and client agree, in real-time, on the client's life habits to change, and agree on the client's personal goals;

f) having the coach transmit to the client, via the Internet, information pertaining to e);

g) having the client transmit to the coach, via the Internet, particularized information pertaining to e), wherein the information includes reportage of events occurring in the life of the client subsequent to e);

h) based on the information received by the coach in step g), having the coach and client work together, in real-time, to help the client take steps toward reaching the client's personal goals;

i) having the client and coach transmit to each other information, via the Internet, pertaining to h);

j) having the client and coach access an Internet file that contains information pertaining to any of c)-i) and that are personal to the client and not accessible by other clients; and k) repeating steps h) and i).

2. The method of claim 1, wherein, in steps f-h), the client and the coach communicate over the Internet at scheduled times, with real-time dialogue in the form of "chat" format typed comments and questions.

3. The method of claim 1, wherein, in steps f-h), the client and the coach communicate over the Internet at scheduled times, with real-time dialogue in the form of Internet-based telephone conversation.

4. The method of claim 1, wherein, in steps f-h), the client and the coach communicate over the Internet at scheduled times, with real-time dialogue in the form of Internet-based video/audio conversation.

5. The method of claim 1, wherein there is provided for the coaches a web-based chat room to which said clients and the general public are denied access.

6. The method of claim 1, wherein the coaching process includes providing to the clients incentives for reaching goals pertaining to the ongoing concern of the clients.

7. The method of claim 6, wherein the incentives include rewards provided to the clients for reaching said goals.

8. The method of claim 6, wherein the incentives include the awarding of points that are redeemable for rewards.

9. The method of claim 1, wherein there is provided for the clients a web-based chat room.

10. The method of claim 9, wherein said clients' chat room is not accessible by the coaches and the general public.

11. The method of claim 1, wherein said method further comprises providing a publicly-accessible Web site that provides information about said coaching method.

12. The method of claim 11, wherein said Web site includes advertising of products or services not sold by the company, wherein entities other than the company pay the company to post said advertising on the Web site.

13. The method of claim 11, wherein products or services are offered for sale on said Web site.

14. The method of claim 1, wherein clients are offered incentives to communicate, via the Internet, with prospective clients of the company about their experience with the coaching program.

15. The method of claim 5, wherein there are periodic visits to the coaches' Web site by non-coach individuals with expertise in the subject of the clients' ongoing concern.

16. The method of claim 9, wherein there are periodic visits to the clients' Web site by non-coach individuals with expertise in the subject of the clients' ongoing concern.

17. The method of claim 1, wherein said ongoing concern of the client pertains to stress.

18. The method of claim 1, wherein said ongoing concern of the client pertains to anxiety.

19. The method of claim 1, wherein said ongoing concern of the client pertains to depression.

20. The method of claim 1, wherein said ongoing concern of the client pertains to pregnancy.

21. The method of claim 1, wherein said ongoing concern of the client pertains to addiction.

22. The method of claim 1, wherein said ongoing concern of the client pertains to menopause.

23. The method of claim 1, wherein said ongoing concern of the client pertains to andropause.

24. The method of claim 1, wherein said ongoing concern of the client pertains to a chronic disease.

25. The method of claim 1, wherein said ongoing concern of the client pertains to elder care.

26. The method of claim 1, wherein said ongoing concern of the client pertains to caring for a disabled person.

27. The method of claim 1, wherein, during steps (f-h), both the client and the coach view monitors which display an electronically-stored file that contains a history of the setting and meeting of the client's goals, and wherein the client and coach communicate via Internet chat, conventional telephony, Internet telephony, or video, or a combination thereof, while said file is displayed.

28. The method of claim 27, wherein the client has access, between coaching sessions, to said electronically-stored file.

29. The method of claim 27, wherein, during steps (f-h), the coach is visible on the monitor of the client while the coach speaks.

30. The method of claim 27, wherein, during steps (f-h), the client's face is visible on the monitor of the coach while the client speaks.

31. The method of claim 29, wherein, during steps (f-h), the client is not shown on the coaches' monitor.

32. The method of claim 29, wherein, during steps (f-h), the client is shown on the coaches' monitor.

* * * * *